United States Patent
Goto et al.

(10) Patent No.: US 9,766,214 B2
(45) Date of Patent: Sep. 19, 2017

(54) SUPERCRITICAL FLUID PROCESSING DEVICE

(71) Applicant: SHIMADZU CORPORATION, Kyoto-shi, Kyoto (JP)

(72) Inventors: Hiroomi Goto, Kyoto (JP); Tsunehiro Inoue, Kyoto (JP); Takahiro Mori, Kyoto (JP); Hirohisa Abe, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 99 days.

(21) Appl. No.: 14/647,333

(22) PCT Filed: Nov. 28, 2012

(86) PCT No.: PCT/JP2012/080753
§ 371 (c)(1),
(2) Date: May 26, 2015

(87) PCT Pub. No.: WO2014/083639
PCT Pub. Date: Jun. 5, 2014

(65) Prior Publication Data
US 2015/0330954 A1    Nov. 19, 2015

(51) Int. Cl.
*G01N 30/00* (2006.01)
*G01N 30/36* (2006.01)
(Continued)

(52) U.S. Cl.
CPC ............ *G01N 30/36* (2013.01); *B01D 15/40* (2013.01); *F16K 31/004* (2013.01); *G01N 30/32* (2013.01);
(Continued)

(58) Field of Classification Search
CPC .. G01N 30/32; G01N 30/36; G01N 2030/025; G01N 2030/328; G05D 7/0641; B01D 15/40
(Continued)

(56) References Cited

U.S. PATENT DOCUMENTS 5,031,448 A    7/1991  Saito
5,224,510 A    7/1993  Pericles
(Continued)

FOREIGN PATENT DOCUMENTS

JP    02-190761 A    7/1990
JP    03-172688 A    7/1991
(Continued)

OTHER PUBLICATIONS

Office Action dated Dec. 15, 2015, issued in counterpart Japanese Patent Application No. 2014-549689, with English translation. (13 pages).
(Continued)

*Primary Examiner* — Benjamin Schmitt
(74) *Attorney, Agent, or Firm* — Westerman, Hattori, Daniels & Adrian, LLP

(57) ABSTRACT

A supercritical fluid chromatograph includes a supercritical flow path, a mobile phase supply section for supplying a mobile phase containing liquid carbon dioxide, a sample introduction section, a sample separation section, a detector, and a pressure control valve. A valve post-stage flow path is connected to a fluid outlet of the pressure control valve, and the inside of the valve post-stage flow path is maintained by pressure maintaining means at a pressure by which a mobile phase from the fluid outlet of the pressure control valve is not vaporized.

7 Claims, 8 Drawing Sheets

(51) Int. Cl.
*G05D 16/20* (2006.01)
*F16K 31/00* (2006.01)
*G05D 7/06* (2006.01)
*B01D 15/40* (2006.01)
*G01N 30/32* (2006.01)

(52) U.S. Cl.
CPC ......... *G05D 7/0641* (2013.01); *G05D 16/202* (2013.01)

(58) Field of Classification Search
USPC ................. 73/61.44, 61.52, 61.55, 61.57
See application file for complete search history.

(56) References Cited

U.S. PATENT DOCUMENTS

| | | | |
|---|---|---|---|
| 5,601,707 | A | 2/1997 | Clay et al. |
| 6,413,428 | B1 | 7/2002 | Berger et al. |
| 2002/0070170 | A1* | 6/2002 | Berger ............... B01D 11/0203 210/656 |
| 2003/0026704 | A1* | 2/2003 | Berger ................ G01N 30/32 417/53 |
| 2008/0010956 | A1* | 1/2008 | Fogelman .......... B01D 11/0203 55/319 |
| 2011/0094606 | A1 | 4/2011 | Kanomata et al. |

FOREIGN PATENT DOCUMENTS

| | | |
|---|---|---|
| JP | 08-338832 A | 12/1996 |
| JP | 2002-071534 A | 3/2002 |
| JP | 2007-133829 A | 5/2007 |
| JP | 2009-544042 A | 12/2009 |
| JP | 2011-118880 A | 6/2011 |
| JP | 2015-509608 A | 3/2015 |
| WO | 2007/055370 A1 | 5/2007 |
| WO | 2008/011416 A2 | 1/2008 |
| WO | 2013/134478 A1 | 9/2013 |

OTHER PUBLICATIONS

International Search Report dated Jan. 8, 2013, issued in corresponding application No. PCT/JP2012/080753, (2 pages).

* cited by examiner

SUPERCRITICAL FLUID PROCESSING DEVICE

TECHNICAL FIELD

The present invention relates to a supercritical fluid processing device such as a supercritical fluid chromatograph or a supercritical fluid extraction device.

BACKGROUND ART

In recent years, supercritical fluid processing devices such as supercritical fluid supercritical fluid chromatography (hereinafter SFC: Supercritical Fluid Chromatography) and a supercritical fluid extraction device (hereinafter SFE: Supercritical Fluid Extraction) that perform analysis and extraction of a sample by using a supercritical fluid are gaining attention. A supercritical fluid has the properties of both a liquid and a gas, and is characteristic in that it has higher diffusivity and lower viscosity than a liquid, and by using the supercritical fluid as a solvent, fast, high-resolution, high-sensitivity analysis, or highly accurate extraction is enabled.

The SFC is chromatography that is performed by applying constant temperature and pressure to carbon dioxide or the like to obtain a supercritical fluid, and by using the supercritical fluid as a solvent. Generally, to keep the solvent in a supercritical state, the flow rate has to be a micro flow rate of 3 ml/min or less, and the pressure of the flow path system has to be 10 MPa or more. Accordingly, an SFC device is provided with a pressure control valve, at a post-stage side of an analytical column, for maintaining the flow path system at a constant pressure of 10 MPa or more. The same thing can be said for the SFE.

As the pressure control valve, those that adopt a method of adjusting a gap (an opening area) between a valve seat provided with an inlet flow path and a valve member clogging the inlet flow path (see Patent Document 1), a method of adjusting the flow path width (an opening area) by driving of a diaphragm (see Patent Document 2), a method of inserting a needle into an orifice opening at an end of an inlet flow path and adjusting the gap (an opening area) based on the insertion depth of the needle into the orifice opening (see Patent Document 3), and the like may be cited.

PRIOR ART DOCUMENTS

Patent Documents

Patent Document 1: Japanese Patent Laid-open Publication No. 2-190761
Patent Document 2: Japanese Patent Laid-open Publication No. 3-172688
Patent Document 3: Japanese Patent Laid-open Publication No. 8-338832

SUMMARY OF THE INVENTION

Problems to be Solved by the Invention

As described above, the SFC and the SFE generally use carbon dioxide as a solvent, and on the upstream side of a valve mechanism portion of a pressure control valve that controls the pressure by a diaphragm, a needle or the like, the pressure of the carbon dioxide is maintained at 10 MPa or more. However, after the carbon dioxide passes through the valve mechanism portion of the pressure control valve, the pressure is drastically reduced to a level similar to the atmospheric pressure, and the carbon dioxide is instantly cooled due to the effect of the heat of vaporization caused by vaporization of the carbon dioxide, and dry ice sometimes occurs near the outlet of the pressure control valve.

When dry ice occurs near the outlet of the pressure control valve, this may lead to damage in the valve member or the valve seat of the valve or may reduce the control by the valve. To prevent this, conventionally, occurrence of dry ice is generally prevented by heating the main body of the pressure control valve by a heater (see Patent Document 2).

For example, during an analysis by the SFC, the flow rate of a mobile phase temporally changes because there are time periods where a sample is included in the mobile phase and where the sample is not included. Also, in the case of using a gradient method of performing an analysis while changing the flow rate of the mobile phase, the flow rate of the mobile phase is changed further significantly. When the mobile phase flow rate changes, the heat of vaporization of carbon dioxide at the outlet portion of the pressure control valve also changes, thereby also changing the heat quantity for cooling, and the fluid temperature at the outlet portion of the pressure control valve is changed. With temperature control of the pressure control valve by a heater, it is difficult to control the inside of the pressure control valve at a constant temperature by causing heating by the heater to follow such instantaneous temperature change. Thus, the temperature of the mobile phase inside the pressure control valve becomes unstable.

The density of carbon dioxide in the supercritical state changes greatly due to a change in the pressure or a change in the temperature compared to carbon dioxide in the state of liquid or gas. As described above, when the temperature of the mobile phase inside the pressure control valve varies due to heating by a heater not being able to follow a change in the temperature of the mobile phase, the density of carbon dioxide inside the pressure control valve also changes greatly. The relationship between a pressure difference $\Delta P$ in front of and behind the valve mechanism portion held by the pressure control valve and the opening area S of the valve mechanism portion is expressed by the following equation by the Bernoulli's principle.

$$\Delta P = Q_m^2 / 2\rho S^2$$

Qm is a fluid flow rate, and $\rho$ is a fluid density. According to this equation, to keep $\Delta P$ constant, a change in the fluid density $\rho$ has to be offset by changing the opening area S, but it is difficult to change the opening area S in accordance with a drastic change in the fluid density $\rho$, and as a result, the pressure control valve cannot control the pressure to be constant, and the analysis result is affected.

Furthermore, an electronic driving mechanism such as a piezo actuator is mounted to the main body of the pressure control valve, and thus, attaching a heater to the main body of the pressure control valve may adversely affect the heat resistance or durability of the electronic driving mechanism.

Accordingly, the present invention has its aim to prevent occurrence of dry ice at an outlet portion of a pressure control valve while stabilizing pressure control by the pressure control valve.

Solutions to the Problems

A supercritical fluid processing device according to the present invention includes a supercritical flow path through which a sample flows together with a mobile phase in a supercritical state, a sample separation section arranged on the supercritical flow path, for performing separation of a sample, a detector arranged on the supercritical flow path, on a downstream side than the sample separation section, the detector being for detecting a sample component separated by the sample separation section, a pressure control valve including a fluid inlet and a fluid outlet, the pressure control valve connected to the supercritical flow path, on a downstream side than the detector, and being for controlling a pressure inside the supercritical flow path to a predetermined pressure and converting a mobile phase flowing through the supercritical flow path into a supercritical state, a valve post-stage flow path having one end connected to the fluid outlet of the pressure control valve, and pressure maintaining means provided to the pressure control valve, on a side of the fluid outlet, the pressure maintaining means being for maintaining inside of the valve post-stage flow path at a pressure by which a mobile phase from the fluid outlet does not vaporize.

Effects of the Invention

According to the supercritical fluid processing device of the present invention, the pressure maintaining means for maintaining the inside of the valve post-stage flow path whose one end is connected to the fluid outlet of the pressure control valve at a pressure by which a mobile phase from the fluid outlet does not vaporize is provided to the pressure control valve, on the fluid outlet side, and thus, vaporization of a mobile phase near the fluid outlet of the pressure control valve is prevented, and generation of dry ice is prevented. Accordingly, since liquid does not vaporize near the pressure control valve, the temperature inside the pressure control valve is not drastically changed, and pressure control by the pressure control valve may be stably performed.

EMBODIMENTS OF THE INVENTION

Figure 1:
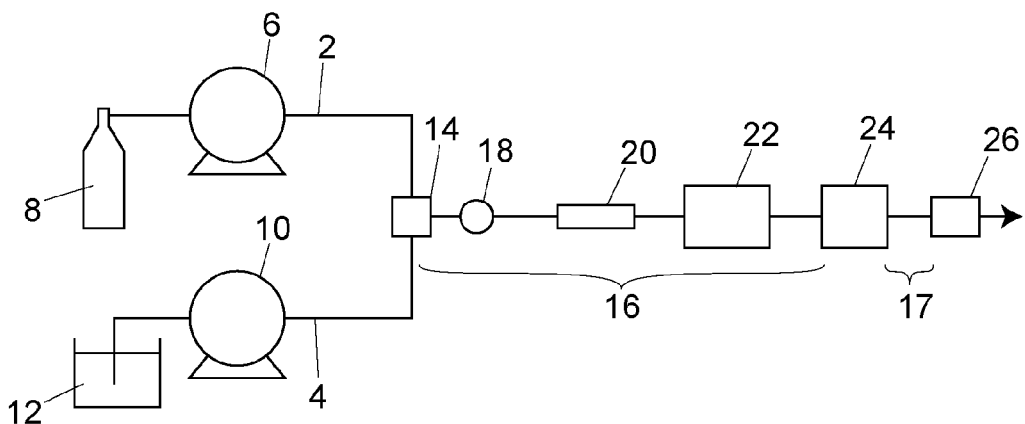
FIG. 1 is a flow path diagram schematically showing an embodiment of a supercritical fluid chromatograph.

Pressure maintaining means of a fluid liquid processing device according to the present invention may be an orifice provided to a valve post-stage flow path.

Further, the pressure maintaining means may be a resistance tube provided as a part of the valve post-stage flow path.

To prevent vaporization of a mobile phase which has flowed into the valve post-stage flow path from a pressure control valve, the pressure inside of the valve post-stage flow path has to be maintained at 7 MPa or more. The pressure inside the valve post-stage flow path is determined by the inner diameter of the pressure maintaining means and the flow rate of a mobile phase. The flow rate of a mobile phase is changed according to the aim of an analysis, but if the variation width of the flow rate is great, an orifice or a resistance tube whose opening area for pressure control is fixed is not able to maintain a desirable pressure in the valve post-stage flow path by which the mobile phase is not vaporized with respect to all the flow rates in the variation width.

Accordingly, in a case where the variation width of the flow rate is great (for example, a difference of two or more digits between the minimum and the maximum), the pressure maintaining means is desirably a second pressure control valve for adjusting the pressure inside the valve post-stage flow path. The inner diameter of the pressure maintaining means may then be adjusted according to the flow rate of the mobile phase.

Now, in the case where there is a pipe on the downstream side of the pressure maintaining means, a problem may arise in that a mobile phase which has passed through the pressure maintaining means is vaporized due to reduction in the pressure, and the pressure maintaining means and the pipe in the periphery are cooled due to the influence of the heat of vaporization, thereby changing the pressure inside the valve post-stage flow path, and generating dry ice inside the valve post-stage flow path and clogging the tube. To prevent this, a supercritical fluid processing device of the present invention desirably further includes heating means for heating the pressure maintaining means. Additionally, in the case where the pressure maintaining means is the second pressure control valve, the pressure control valve is to be heated by the heating means, but the second pressure control valve is not for controlling the pressure inside the tube with high accuracy, and there is no need to mount a precise actuator such as a piezo actuator for dynamically controlling the valve. Accordingly, unlike the pressure control valve for controlling the pressure of a supercritical flow path, even if the second pressure control valve is heated by the heating means, the influence of the heat on the mechanism of the actuator for driving the second pressure control valve is small.

Further, an orifice as the pressure maintaining means may be provided at the downstream end of the valve post-stage flow path, and the downstream end of the valve post-stage flow path may be exposed to air. By ejecting carbon dioxide from the orifice portion into the air, the ejected carbon dioxide is vaporized in the air, and the pipe is not cooled by the heat of vaporization. Accordingly, there is no need to provide the heating means for heating the pressure maintaining means and the pipe in the periphery. Additionally, "exposure to air" here includes a case where a mobile phase which has passed through the orifice is ejected into a closed space which is large enough to be considered equivalent to being exposed to air.

Figure 8:
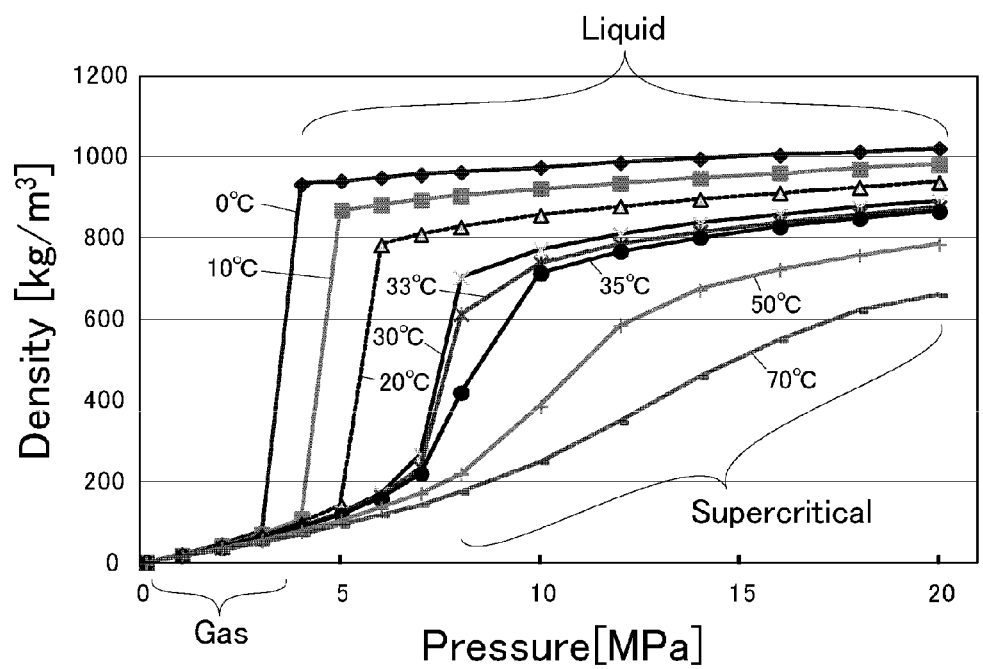
FIG. 8 is a graph showing the relationship between the pressure and density of carbon dioxide on the temperature basis.

Furthermore, cooling means for cooling a flow path connected to a fluid inlet of the pressure control valve to thereby convert a mobile phase that flows to the fluid inlet into a liquid state is desirably further provided. As shown in FIG. 8, the density of carbon dioxide in a supercritical state changes greatly when the pressure changes, but the density of carbon dioxide in a liquid state under the pressure of 4 MPa or more does not change much even when the pressure changes. Thus, by causing a mobile phase to pass through the pressure control valve in a liquid state, a change in the density of the mobile phase caused by a change in the pressure of the mobile phase due to passing through the pressure control valve may be made small, and pressure control by the pressure control valve may be further stabilized.

An embodiment of a supercritical fluid chromatograph, which is one type of the supercritical fluid processing device, will be described with reference to FIG. 1.

A carbon dioxide delivery flow path 2 for delivering carbon dioxide in a liquid state by a pump 6, and a methanol delivery flow path 4 for delivering methanol, which is a modifier, by a pump 10 are connected to a mixer 14. A supercritical flow path 16 is connected to the mixer 14. A sample injection section (autosampler) 18 for injecting a sample into the supercritical flow path 16, a separation column (sample separation section) 20, a detector 22, and a pressure control valve 24 are arranged on the supercritical flow path 16.

Carbon dioxide and methanol are mixed at the mixer 14, and are introduced into the supercritical flow path 16 as a mobile phase. The carbon dioxide delivery flow path 2, the methanol delivery flow path 4, and the mixer 14 form a mobile phase supply section for delivering, as a mobile phase, a solvent obtained by mixing carbon dioxide and methanol. The internal pressure of the supercritical flow path 16 is controlled by the pressure control valve 24 to be 7 MPa or more, and a mobile phase that is introduced into the supercritical flow path 16 falls into a supercritical state. A sample injected by the sample injection section 18 is delivered to the separation column 20 by the mobile phase in the supercritical state, and is separated into components and discharged to the outside via the detector 22, the pressure control valve 24, and the pressure maintaining means 26.

Additionally, as mobile phases, those of only carbon dioxide, a mixture of carbon dioxide and alcohol such as methanol, and a mixture of carbon dioxide and a solvent used in a high performance liquid chromatograph, such as acetonitrile or dichloromethane, may be used.

Figure 2:
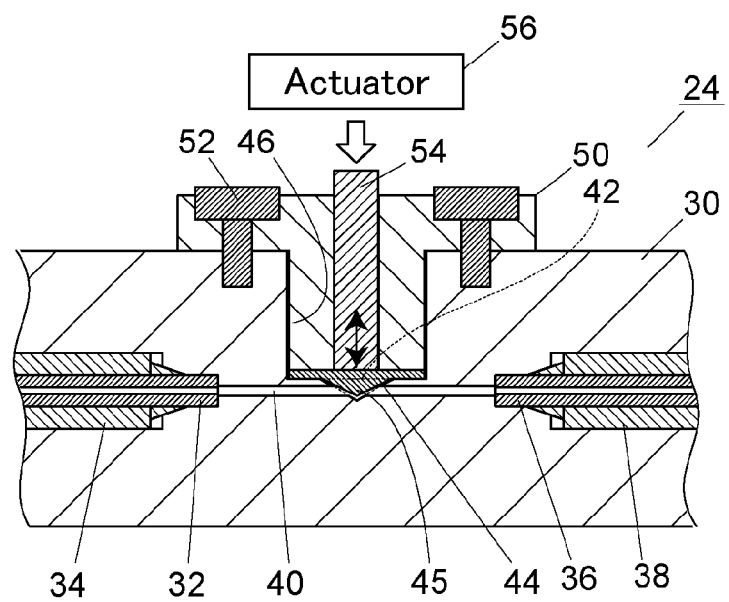
FIG. 2 is a cross-sectional diagram showing an example of a pressure control valve of the embodiment.

An example of the pressure control valve 24 will be described with reference to FIG. 2.

The pressure control valve 24 variably adjusts the gap between a concave section 42 that divides a linear internal flow path 40 provided inside a pressure control block 30 and a protrusion section 45 fitted in the concave section 42. Holes for fixing pipes 32 and 36 by male nuts 34 and 38, respectively, are provided on the side surfaces of the pressure control block 30. The pipe 32 forms a part of the supercritical flow path 16, and the pipe 36 forms a valve post-stage flow path 17 described later. The pipe 32 is connected to one end of the internal flow path 40, and the pipe 36 is connected to the other end of the internal flow path 40. One end of the internal flow path 40 forms a fluid inlet, and the other end of the internal flow path 40 forms a fluid outlet. The male nuts 34 and 38 are members having threads tapped on the outer circumferential surfaces, and are attached to the pipes 32 and 36, respectively, by ferrules. Threads for being screwed with the threads on the outer circumferential surfaces of the male nuts 34 and 38 are tapped on the inner circumferential surfaces of the holes for fixing the pipes 32 and 36.

The plane shape of a sealing member 44 for adjusting the opening area of the internal flow path 40 is a circle, and the protrusion section 45 is provided at the center. The sealing member 44 has the protrusion section 45 inserted, facing the internal flow path 40, into a circular hole 46 provided to a plane of the pressure control block 30 which is parallel to the internal flow path 40. The concave section 42 having a cone shape is provided in such a way as to cross the internal flow path 40 from the center portion of the bottom surface of the hole 46, and the protrusion section 45 is fitted in the concave section 42. The sealing member 44 is formed of a material having chemical resistance, pressure resistance, elasticity, and impact resistance, such as ultra-high molecular weight polyethylene or polyetheretherketone.

A tip end portion of a sealing member pressing tool 50 is also inserted in the hole 46. The sealing member pressing tool 50 is for pressing, with its tip end portion, a peripheral edge portion of the sealing member 44 against the bottom surface of the hole 46 and for preventing leakage of a mobile phase flowing through the internal flow path 40 from the concave section 42. A base end of the sealing member pressing tool 50 has a larger outer diameter than the tip end portion to be inserted into the hole 46, and the base end portion is fixed to the pressure control valve 24 by screws 42.

A through hole is provided at the center portion of the plane of the sealing member pressing tool 50, and a columnar driving member 54 penetrates the through hole. A tip end of the driving member 54 is in contact with the center portion of the sealing member 44 positioned on the backside of the protrusion section 42. For example, the driving member 54 is vertically driven by an actuator 56, such as a piezo actuator, and thereby changes the shape of the sealing member 44 and adjusts the gap between the tip end of the protrusion section 45 and the recessed section 42.

Additionally, the structure of the pressure control valve 24 is not limited to that described above, and any structure may be used as long as the pressure inside the supercritical flow path 16 may be controlled.

Referring back to FIG. 1, the valve post-stage flow path 17 is connected and the pressure maintaining means 26 is provided on the outlet side of the pressure control valve 24. The pressure maintaining means 26 is for maintaining the pressure inside the valve post-stage flow path 17 at a pressure by which a mobile phase does not vaporize.

Figure 3:
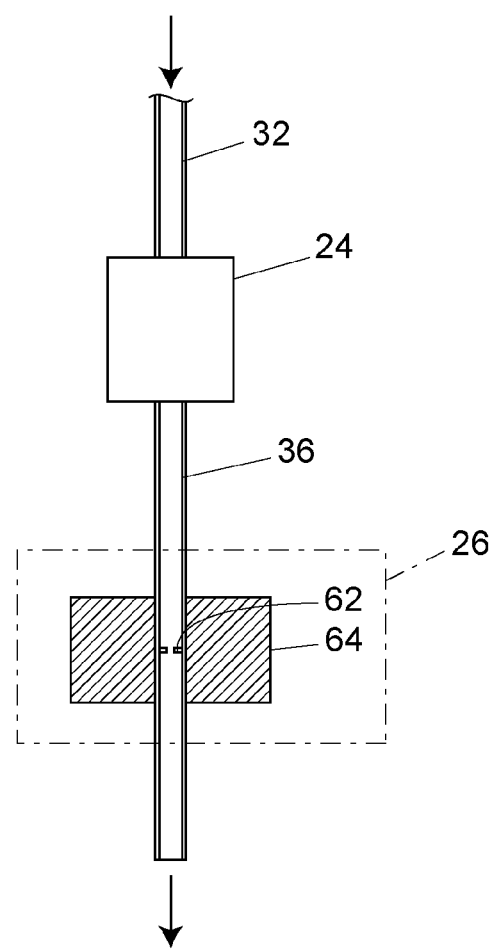
FIG. 3 is a cross-sectional diagram schematically showing an embodiment of pressure maintaining means.

As an example of the pressure maintaining means 26, an orifice section 62 provided to the pipe 36 forming the valve post-stage flow path 17 may be cited, as shown in FIG. 3. In this case, to prevent drastic cooling of the pipe 36 due to vaporization of a mobile phase which has passed through the orifice section 62 caused by the reduction in the pressure, a heater (heating means) 64 is provided for heating the part of the pipe 36 where the orifice section 62 is provided.

Figure 4:
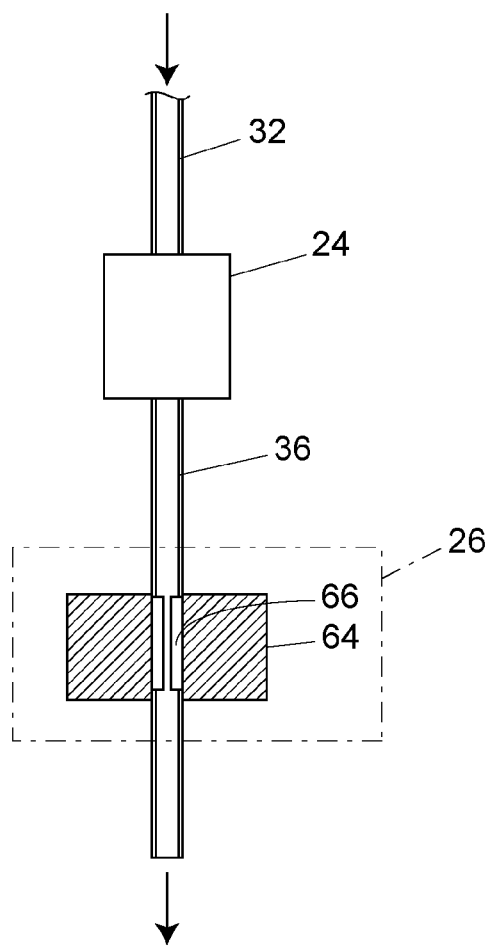
FIG. 4 is a cross-sectional diagram schematically showing another embodiment of the pressure maintaining means.

As another example of the pressure maintaining means 26, a resistance tube 66 provided as a part of the valve post-stage flow path 17 may be cited, as shown in FIG. 4. Also in this case, the heater 64 is needed to prevent drastic cooling of the pipe 36 due to vaporization of a mobile phase which has passed through the resistance tube 66 caused by the reduction in the pressure.

Figure 5:
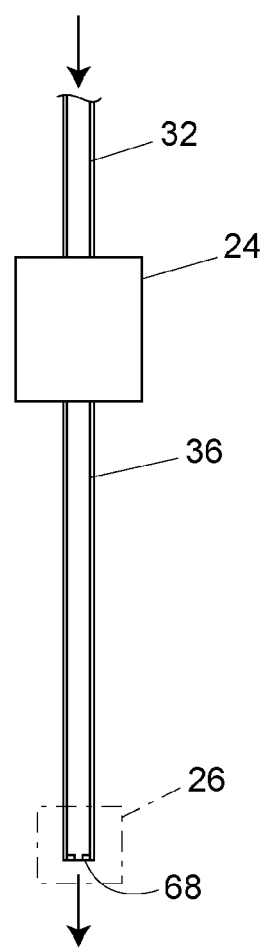
FIG. 5 is a cross-sectional diagram schematically showing further another embodiment of the pressure maintaining means.

As further another example of the pressure maintaining means 26, an orifice section 68 provided at the downstream end of the pipe 36 may be cited, as shown in FIG. 5. The downstream end of the pipe 36 to which the orifice section 68 is provided is exposed to air. In this case, a heater for heating the part of the pipe 36 where the orifice section 68 is provided is not necessary.

Figure 9A:
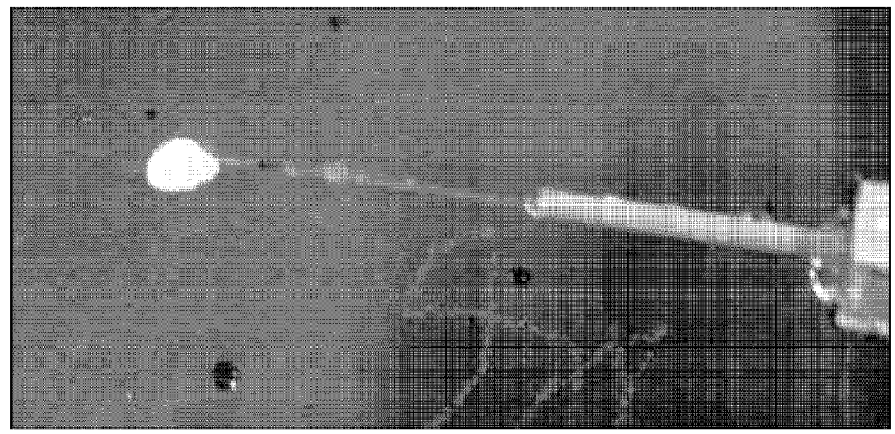
FIGS. 9A and 9B are images showing a result of studying an effect of the embodiment in FIG. 5.
Figure 9B:
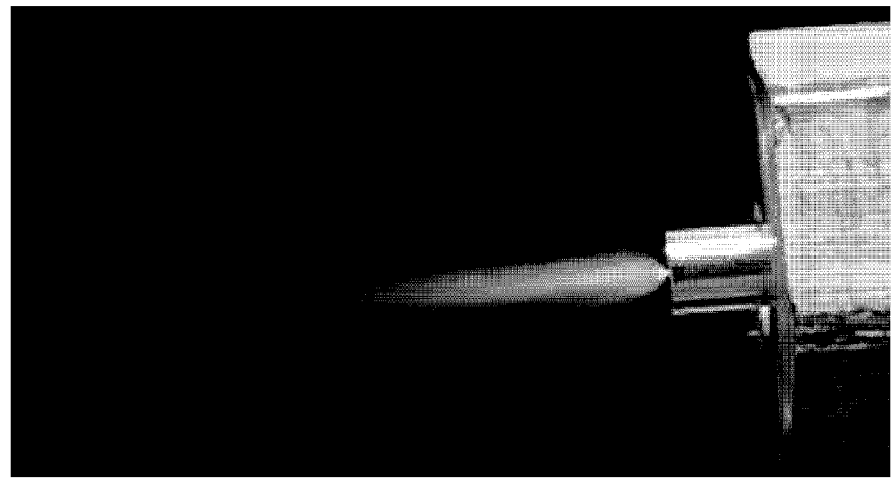

FIGS. 9A and 9B are images obtained by studying an effect of providing the orifice section 68 at the downstream end of the pipe 36. FIG. 9A shows the state of a mobile phase that is discharged from the downstream end of a resistance tube where a resistance tube having an inner diameter of 30

μm is connected at the downstream end of the pipe 36, and FIG. 9B shows the state of a mobile phase that is discharged from an orifice section where the orifice section 68 having an inner diameter of 50 μm is provided at the downstream end of the pipe 36.

As can be seen from the images in FIGS. 9A and 9B, when a resistance tube is connected at the downstream end of the pipe 36, the pressure in the resistance tube linearly decreases until the outlet is at the atmospheric pressure, and thus, cooling due to the heat of vaporization of carbon dioxide occurs along the resistance tube, and dry ice is precipitated at the outlet of the resistance tube. In contrast, with the orifice section 68 being provided at the downstream end of the pipe 36 and the downstream end of the pipe 36 being exposed to air, carbon dioxide that is ejected from the orifice section 68 vaporizes in the air, and thus, vaporization of carbon dioxide does not occur inside the pipe 36 and cooling of the pipe 36 by the heat of vaporization is prevented, and dry ice is not precipitated from the orifice section 68. Accordingly, a heater for heating the pipe 36 is not necessary.

Figure 6:
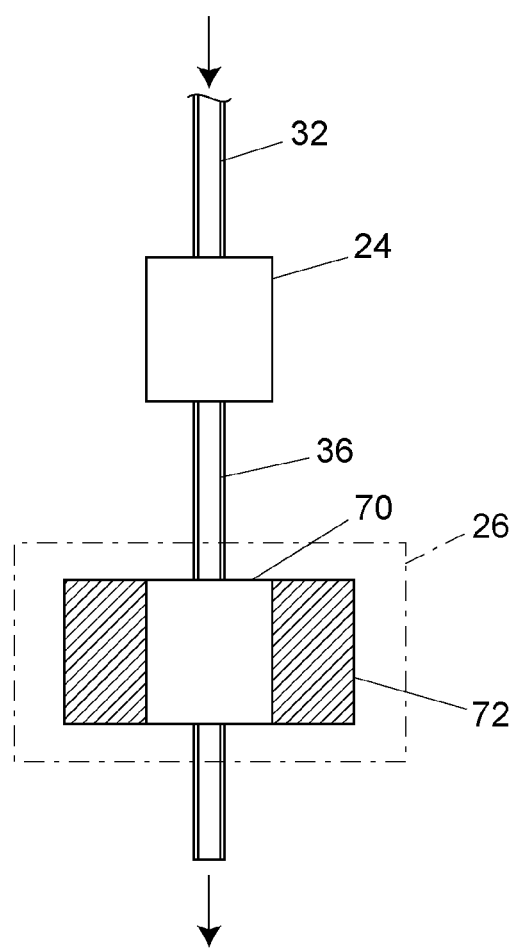
FIG. 6 is a cross-sectional diagram schematically showing still another embodiment of the pressure maintaining means.

Furthermore, as shown in FIG. 6, a second pressure control valve 70 may be used as the pressure maintaining means 26. Especially with a device where the flow rate of a mobile phase changes in a wide range of two or more digits, if the opening area of an orifice, a resistance tube or the like for pressure control is fixed, it is not possible to maintain, in all of the wide flow rate range, the inside of the pipe 36 at a desirable pressure where a mobile phase is not vaporized.

For example, in the case where the flow rate of a mobile phase is to be changed in the range of 0.1 ml/min to 10 ml/min, if an orifice or a resistance tube that maintains the pressure of 7 MPa when the flow rate is 0.1 ml/min is used as the pressure maintaining means 26, pressure of 20 MPa is maintained when the flow rate is 10 ml/min, and the function of pressure control for the inside of the supercritical flow path 18 by the pressure control valve 24 is achieved only in the region of 20 MPa or more. On the other hand, if a resistance tube that maintains the pressure of 7 MPa when the flow rate is 10 ml/min is used as the pressure maintaining means, the inside of the pipe 36 cannot be maintained at a high pressure when the flow rate is 0.1 ml/min, and vaporization of carbon dioxide occurs at the fluid outlet of the pressure control valve 24.

In the case where the variation width of the flow rate of a mobile phase is great (for example, a difference of two or more digits between the minimum and the maximum), it is desirable to use, as the pressure maintaining means 26, the second pressure control valve 70, which is capable of variably adjusting the opening area for pressure control in the pipe 36. The second pressure control valve 70 may have a similar or different structure from the pressure control valve 24, and any structure is allowed as long as the pressure inside the pipe 36 may be variably adjusted. Unlike the pressure control valve 24, the second pressure control valve 70 does not need dynamic control for pressure stabilization at the time of analysis, and does not need highly precise control. Additionally, also in this case, a heater 72 is needed to prevent the pipe 36 from being drastically cooled due to a mobile phase which has passed through the second pressure control valve 70 being vaporized due to reduction in the pressure.

Figure 7:
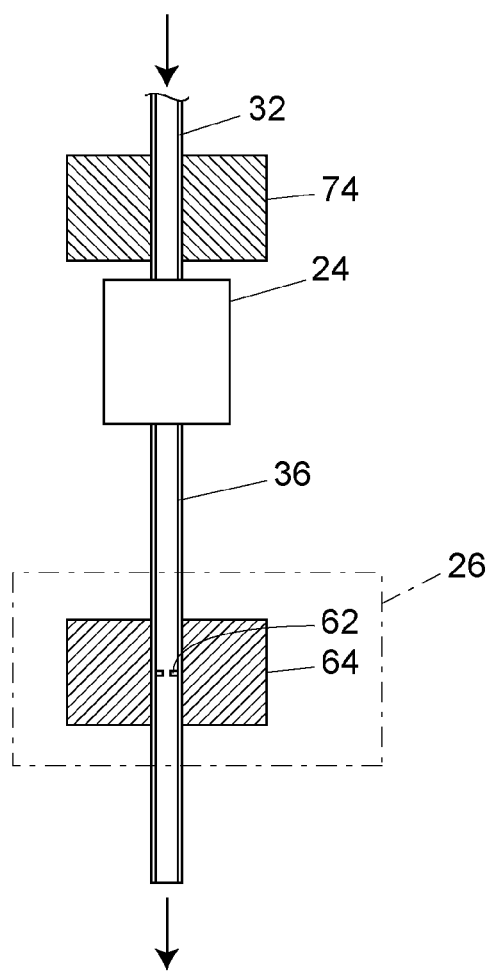
FIG. 7 is a cross-sectional diagram schematically showing an embodiment where cooling means is provided on the upstream side of a pressure control valve.

Furthermore, FIG. 7 schematically shows an embodiment where cooling means 74 is provided on the upstream side of the pressure control valve 24. As the cooling means 74, a Peltier device, for example, may be used. A mobile phase in a supercritical state which has been heated by a column oven or the like is cooled to 30° C. or less by the cooling means 74 and is converted into a liquid state, and is then caused to pass through the pressure control valve 24. A change in the density of carbon dioxide in a liquid state with respect to a change in the pressure is small compared to a mobile phase in a supercritical state, and thus, a change in the density due to a change in the pressure at the time of passing through the pressure control valve 24 may be suppressed. Additionally, the embodiment shown in FIG. 7 is the embodiment in FIG. 3 to which the cooling means 74 is added, but the present invention is not limited thereto, and the cooling means 74 may be added to the structure of the embodiment in FIG. 4, 5 or 6.

DESCRIPTION OF REFERENCE SIGNS

2: Carbon dioxide delivery flow path
4: Methanol delivery flow path
6, 10: Pump
8: Carbon dioxide
12: Methanol (modifier)
14: Mixer
16: Supercritical flow path
17: Valve post-stage flow path
18: Sample injection section
20: Separation column
22: Detector
24: Pressure control valve
26, 26a, 26b, 26c: Pressure maintaining means
30: Pressure control block
32, 36: Pipe
34, 38: Male nut
40: Internal flow path
42: Concave section
44: Sealing member
45: Protrusion section (sealing member)
46: Sealing member fitting hole
50: Sealing member pressing tool
52: Screw
54: Driving member
56: Actuator
62, 68: Orifice section
64, 72: Heating means
66: Resistance tube
70: Second pressure control valve
74: Cooling means

What is claimed is:
1. A supercritical fluid processing device comprising:
a supercritical flow path through which a sample flows together with a mobile phase in a supercritical state;
a sample separation section arranged on the supercritical flow path, for performing separation of the sample;
a detector arranged on the supercritical flow path, on a downstream side of the sample separation section, the detector being for detecting a sample component separated by the sample separation section;
a pressure control valve connected to the supercritical flow path on a downstream side of the detector, the pressure control valve having a fluid inlet and a fluid outlet, and being for controlling a pressure inside the supercritical flow path to a predetermined pressure and for converting a mobile phase into a supercritical state;
a valve post-stage flow path having one end connected to the fluid outlet of the pressure control valve; and
pressure maintaining means provided to the pressure control valve, on a side of the fluid outlet, the pressure maintaining means being for maintaining an inside of the valve post-stage flow path at a pressure by which a mobile phase from the fluid outlet does not vaporize;

wherein no heaters are provided between the fluid outlet of the pressure control valve and the pressure maintaining means.

2. The supercritical fluid processing device according to claim 1, wherein the pressure maintaining means is an orifice provided to the valve post-stage flow path.

3. The supercritical fluid processing device according to claim 1, wherein the pressure maintaining means is a resistance tube provided as a part of the valve post-stage flow path.

4. The supercritical fluid processing device according to claim 1, wherein the pressure maintaining means is a second pressure control valve for adjusting a pressure inside the valve post-stage flow path.

5. The supercritical fluid processing device according claim 1, further comprising heating means for heating the pressure maintaining means.

6. The supercritical fluid processing device according to claim 2, wherein the orifice is provided at a downstream end of the valve post-stage flow path, and the downstream end of the valve post-stage flow path is exposed to air.

7. The supercritical fluid processing device according to-claim 1, further comprising cooling means for converting a mobile phase flowing to the fluid inlet into a liquid state by cooling a flow path connected to the fluid inlet of the pressure control valve.

* * * * *